US012653932B2

(12) United States Patent
Höner et al.

(10) Patent No.: US 12,653,932 B2
(45) Date of Patent: Jun. 16, 2026

(54) BREASTPUMP UNIT AND METHOD OF OPERATION

(71) Applicant: MEDELA AG, Baar (CH)

(72) Inventors: Sebastian Höner, Zurich (CH); Jakub Piotr Pawlowski, Zug (CH)

(73) Assignee: MEDELA AG, Baar (CH)

( * ) Notice: Subject to any disclaimer, the term of this patent is extended or adjusted under 35 U.S.C. 154(b) by 909 days.

(21) Appl. No.: 17/801,233

(22) PCT Filed: Feb. 19, 2021

(86) PCT No.: PCT/IB2021/051409
§ 371 (c)(1),
(2) Date: Aug. 19, 2022

(87) PCT Pub. No.: WO2021/165892
PCT Pub. Date: Aug. 26, 2021

(65) Prior Publication Data
US 2022/0409782 A1     Dec. 29, 2022

(30) Foreign Application Priority Data
Feb. 21, 2020     (AU) ................................. 2020900501

(51) Int. Cl.
  *A61M 1/06*          (2006.01)
  *A61M 1/00*          (2006.01)
(52) U.S. Cl.
  CPC .............. *A61M 1/064* (2014.02); *A61M 1/75* (2021.05)
(58) Field of Classification Search
  CPC ........ A61M 1/06–1/0697; A61M 1/75; A61M 1/74
  See application file for complete search history.

(56) References Cited

U.S. PATENT DOCUMENTS 2,542,505 A * 2/1951 Gascoigne .............. A61M 1/06
                                                    604/74
4,249,481 A * 2/1981 Adams .................... A61M 1/06
                                                    119/14.47
(Continued)

FOREIGN PATENT DOCUMENTS

AU        2016421331 A1     3/2019
CN        101730554 A       6/2010
(Continued)

OTHER PUBLICATIONS

China Office Action for Application No. 202180015370.0, dated May 15, 2025.
(Continued)

*Primary Examiner* — Cris L. Rodriguez
(74) *Attorney, Agent, or Firm* — MARSHALL, GERSTEIN BORUN LLP

(57) ABSTRACT

A method for operating a breastpump unit for expression of human breastmilk and a breastpump unit. The breastpump unit having a pump assembly for generating vacuum pressure, a reservoir for receiving breastmilk, and a breast shield for sealing application to a breast to be pumped. The breast shield has a flexible inner chamber for receiving a nipple of the breast and a second chamber, in particular an outer chamber extending about the outside of the inner chamber and which at least partially surrounds a nipple that is inserted into the inner chamber. The method includes a cycle including evacuating the inner chamber and the reservoir by the pump assembly to a first vacuum pressure, connecting the second chamber to the pump assembly and to the reservoir 24 and evacuating the second chamber to a second vacuum pressure, in which the second vacuum pressure is higher or greater than the first vacuum pressure, and at least partly releasing the vacuum from the second chamber to a lower
(Continued)

vacuum pressure, in particular lower than the first vacuum pressure.

20 Claims, 6 Drawing Sheets

(56) References Cited

U.S. PATENT DOCUMENTS

| | | | | |
|---|---|---|---|---|
| 4,263,912 A * | 4/1981 | Adams | A61M 1/0697 | 604/75 |
| 4,772,262 A * | 9/1988 | Grant | A61M 1/06935 | 604/74 |
| 4,799,922 A * | 1/1989 | Beer | A61M 1/066 | 604/74 |
| 5,049,126 A * | 9/1991 | Larsson | A61M 1/064 | 604/74 |
| 6,663,587 B2 * | 12/2003 | Silver | A61M 1/0697 | 604/74 |
| 6,673,037 B1 * | 1/2004 | Silver | A61M 1/066 | 604/74 |
| 6,932,790 B2 * | 8/2005 | McKendry | A61M 1/06 | 604/74 |
| 6,964,651 B1 * | 11/2005 | McKendry | A61M 1/0697 | 604/74 |
| 6,974,439 B1 * | 12/2005 | McKendry | A61M 1/066 | 604/74 |
| 7,166,087 B2 * | 1/2007 | Silver | A61M 1/066 | 604/74 |
| 7,354,418 B2 * | 4/2008 | Lee | A61M 1/066 | 604/74 |
| 7,381,197 B2 * | 6/2008 | Kelly | A61M 1/06 | 604/74 |
| 8,052,635 B1 * | 11/2011 | Kelly | A61M 1/75 | 604/74 |
| 8,070,715 B2 | 12/2011 | Quackenbush et al. | | |
| 8,398,584 B2 * | 3/2013 | Britto | A61M 1/06 | 604/74 |
| 8,523,804 B2 | 9/2013 | Cudworth | | |
| 8,591,458 B2 * | 11/2013 | Britto | A61M 1/064 | 604/74 |
| 8,961,454 B2 * | 2/2015 | Chen | A61M 1/066 | 604/74 |
| 9,603,982 B2 * | 3/2017 | Silver | A61M 1/0697 | |
| 10,258,723 B2 | 4/2019 | Garbez et al. | | |
| 10,449,273 B2 | 10/2019 | Aalders | | |
| 11,904,077 B2 | 2/2024 | Schlienger et al. | | |
| 2003/0004459 A1 * | 1/2003 | McKendry | A61M 1/06 | 604/74 |
| 2003/0191433 A1 * | 10/2003 | Prentiss | A61M 1/06935 | 604/74 |
| 2004/0024351 A1 | 2/2004 | Greter et al. | | |
| 2004/0181187 A1 * | 9/2004 | Warburton | A61M 1/066 | 604/74 |
| 2005/0154348 A1 * | 7/2005 | Lantz | A61M 1/0697 | 604/74 |
| 2005/0154349 A1 * | 7/2005 | Renz | A61M 1/82 | 604/74 |
| 2005/0234370 A1 * | 10/2005 | Beal | A61M 1/06 | 604/74 |
| 2007/0060873 A1 * | 3/2007 | Hiraoka | A61M 1/82 | 604/74 |
| 2008/0177224 A1 * | 7/2008 | Kelly | A61M 1/06 | 604/74 |
| 2009/0024080 A1 * | 1/2009 | Rohrig | A61M 1/0697 | 604/74 |
| 2009/0099511 A1 | 4/2009 | Sutrina et al. | | |
| 2010/0121266 A1 * | 5/2010 | Bryan | A61M 1/06935 | 604/74 |
| 2011/0071466 A1 * | 3/2011 | Silver | A61M 1/064 | 604/74 |
| 2014/0052056 A1 * | 2/2014 | Garbez | A61M 1/067 | 604/74 |
| 2014/0121593 A1 * | 5/2014 | Felber | A61M 1/0697 | 604/74 |
| 2014/0378946 A1 | 12/2014 | Thompson et al. | | |
| 2015/0065994 A1 * | 3/2015 | Fridman | A61M 1/0697 | 604/74 |
| 2015/0314053 A1 * | 11/2015 | Furrer | A61M 1/066 | 604/74 |
| 2016/0000980 A1 * | 1/2016 | Alvarez | A61M 1/062 | 604/74 |
| 2018/0008758 A1 | 1/2018 | Garbez et al. | | |
| 2021/0252201 A1 * | 8/2021 | Post | A61M 1/0697 | |
| 2021/0361837 A1 * | 11/2021 | Bijoor | A61M 1/0693 | |
| 2023/0124979 A1 * | 4/2023 | Larsson | A61M 1/06 | 604/74 |
| 2023/0173148 A1 * | 6/2023 | Nagy-Gannon | A61M 1/064 | 604/74 |

FOREIGN PATENT DOCUMENTS

| | | |
|---|---|---|
| CN | 102481395 A | 5/2012 |
| CN | 102657902 A | 9/2012 |
| CN | 103480052 A | 1/2014 |
| CN | 105431182 A | 3/2016 |
| CN | 108079392 A | 5/2018 |
| CN | 109414532 A | 3/2019 |
| CN | 111263648 A | 6/2020 |
| EP | 2111882 A1 | 10/2009 |
| EP | 2687246 A1 | 1/2014 |
| EP | 3027240 A1 | 6/2016 |
| IN | 201647041948 A | 12/2016 |
| JP | 2009-028557 A | 2/2009 |
| WO | WO-2013-184004 A1 | 12/2013 |
| WO | WO-147577 A1 | 1/2014 |
| WO | WO-2015/014643 A1 | 2/2015 |
| WO | WO-2019080995 A1 * | 5/2019 .............. A61M 1/06 |

OTHER PUBLICATIONS

Notice of Allowance for Chinese Patent Application No. 202180015370. 0, dated Aug. 11, 2025.
International Search Report for PCT/IB2021/051409 dated Apr. 29, 2021.

* cited by examiner

S2    S4

0 mm Hg

-200 mm Hg

-380 mm Hg

S1    S3

INNER CHAMBER 15

OUTER CHAMBER 16

10

34

35

28

30

26

29

36    16

22

11  15

24

BREASTPUMP UNIT AND METHOD OF OPERATION

PRIORITY CROSS-REFERENCE

The present application is the US national phase of International Patent Application No. PCT/IB2021/051409, filed Feb. 19, 2021, which claims priority from Australian Provisional Patent Application No. 2020900501 filed 21 Feb. 2020 the contents of which is to be considered to be incorporated into this specification by this reference.

TECHNICAL FIELD

The present invention relates to a breastpump, or a breastpump unit for expressing human breastmilk and to a method of operating a breastpump, or a breastpump unit. Hereinafter, reference to a breastpump unit will be made rather than referring to a breastpump, or a breastpump unit throughout this specification.

BACKGROUND OF INVENTION

The discussion of the background to the invention that follows is intended to facilitate an understanding of the invention. However, it should be appreciated that the discussion is not an acknowledgement or admission that any aspect of the discussion was part of the common general knowledge as at the priority date of the application.

Breastpump units are known in the prior art and comprise manually operated and motor driven units. The motor driven units can be connected to a mains electricity supply or can be battery-operated. The motor driven units include a vacuum pump and one or two breastshields for placement on the mother's breast or breasts. Breastpump units aim to simulate the manner in which a baby suckles a mother's breast and so breastpump units thus pump in a cyclic manner using vacuum to apply and release pressure to the breast and nipple through the breastshield and to create a vacuum within the or each breastshield to draw milk from the mother's breast. Breastpump units include a milk collection container into which milk drawn from the mother's breast can be captured and stored for later use.

Breastshields themselves are provided in a large number of different forms which are intended to ensure comfortable fitting on different sized and shaped breasts, but common to breastshields is their flexible nature that allows them to pulse or pulsate in contact with the nipple and sometimes the breast about the nipple, to extract the milk. That is, the breastshield is flexible at least in the section of the breastshield in which the nipple is inserted and the nipple is thus squeezed and relaxed cyclically to promote the expression of milk. Pulsation is generated by creating and releasing a vacuum within the breastshield.

Traditionally, the capacity of the vacuum pump would determine level of vacuum generated within the breastshield. Also, the capacity of the vacuum pump would determine the speed at which the required vacuum is reached. Larger vacuum pumps can therefore deliver greater vacuum more quickly than smaller vacuum pumps. However, for breastpump units, space and weight are factors in selecting a vacuum pump, as is energy use (mainly for battery operated units) and noise generation. For these parameters, smaller vacuum pumps are usually preferred.

One example of a method of operating a breastpump unit is disclosed in EP 3 027 240 in the name of Koninklijke Philips N. V., which discloses an apparatus and method for evacuating a system, applicable for use in a breastpump device. The system of EP 3 027 240 purports to generate an increased vacuum over what can be achieved by the vacuum pump alone. The system generates vacuum in a pressure chamber (a milk collection bottle for example) and a separate pressure tank by connecting the inlet of the vacuum pump to the pressure chamber and the pressure tank and connecting the outlet of the vacuum pump to atmosphere. The vacuum pump evacuates both of the pressure chamber and the pressure tank to the same vacuum. When the maximum vacuum has been reached, the system of EP 3 027 240 switches the outlet of the vacuum pump into connection with the inlet of the pressure tank, so that the pressure at the outlet of the vacuum pump is at the vacuum generated in the pressure tank rather than at atmosphere. This allows the vacuum pump to generate increased vacuum in the pressure chamber and so allows the system to generate a greater vacuum than possible with just the vacuum pump alone. When the vacuum is to be released, a release valve is triggered to exhaust both of the pressure chamber and the pressure tank to atmosphere.

The system of EP 3 027 240 thus purports to enable a higher or greater vacuum to be generated from a vacuum pump that is not rated to generate such a level of vacuum and thus allows the use of smaller and less expensive vacuum pumps. However, a drawback of the system of EP 3 027 240 is the requirement for both a pressure chamber and a pressure tank for achieving the increase in vacuum pressure over that which can be generated alone by the vacuum pump. When used in a breast pump device, the tank undesirably adds complexity and bulk.

The present invention aims to provide improved breastpump units and methods of operating breastpump units.

SUMMARY OF THE INVENTION

According to the present invention there is provided a method for operating a breastpump unit for expression of human breastmilk, the breastpump unit having:
 a. a pump assembly for generating vacuum pressure,
 b. a reservoir for receiving breastmilk, and
 c. a breast shield for sealing application to a breast to be pumped, the breast shield having a flexible inner chamber for receiving a nipple of the breast and a second chamber, in particular an outer chamber extending about the outside of the inner chamber and which at least partially surrounds a nipple that is inserted into the inner chamber,
the method comprising a cycle that is characterized by the steps, in order of:
 i. evacuating the inner chamber and the reservoir by the pump assembly to a first vacuum pressure,
 ii. connecting the second chamber to the pump assembly and to the reservoir and evacuating the second chamber to a second vacuum pressure, in which the second vacuum pressure is higher than the first vacuum pressure, and
 iii. at least partly releasing the vacuum from the second chamber to a lower pressure, in particular lower than the first vacuum pressure.

The inner chamber is flexible so that it can compress or squeeze a nipple that is inserted into it for the purpose of breastmilk expression. Cyclic compression and release of the nipple through the method of the invention facilitates improved breastmilk expression, both in terms of the efficiency of expression and in the comfort experienced by the mother.

The inner chamber can be formed by a flexible liner that includes an entry portion for receipt of a nipple and in some forms of the invention, the inner diameter of the entry portion is less than the outer diameter of the nipple of the mother that the breastpump unit is being used with. This means that once the nipple is inserted into the entry portion, the nipple is naturally compressed or squeezed by the inner liner in the at rest or relaxed state of the inner chamber. By the method of the invention, the natural compression that is applied to the nipple can be reduced or completely released by the vacuum that is introduced into the second chamber in step ii above, which causes the inner chamber, in particular the entry portion of the inner liner, to expand. The application and release or reduction of that vacuum can thus apply a cycle of compression and relaxation to the nipple for the purpose of breastmilk extraction. In this form of the invention, initial insertion of a nipple into the entry portion of the inner liner can be facilitated by an initial introduction of vacuum into the second chamber to expand the entry portion and thereafter that vacuum can be released or reduced for the inner liner to engage or grip the nipple prior to the method of the invention commencing for breastmilk expression. The inner liner can be an annular or tubular liner.

In other forms of the invention, the inner diameter of the entry portion is about the same as, or greater than the outer diameter of the nipple of the mother that the breastpump unit is being used with. This means that once the nipple is inserted into the entry portion, the inner liner needs to be contracted for the compressed or squeezed.

The second chamber can be stiff or rigid, but at least should be less flexible, or more inflexible than the inner chamber.

The first vacuum pressure that is applied to the inner chamber is applied to draw or extract milk through the nipple for discharge to the reservoir. The first vacuum pressure can be a constant pressure and in prototype testing to date, a pressure of about −200 mmHg has been employed. The vacuum pressure within the second chamber can cycle or fluctuate about the first vacuum pressure. The first vacuum pressure will tend to collapse or contract the inner chamber until the vacuum pressure within the second chamber reaches the same pressure as the first vacuum pressure and thereafter, the vacuum pressure within the second chamber will tend to expand the inner chamber, in particular the entry portion of the inner liner as the vacuum pressure within the second chamber progresses to the second vacuum pressure, thus releasing pressure on the nipple. The squeezing and release of the nipple in this way has been found to promote good milk flow through the nipple, with reduced propensity for blocked milk ducts and the formation of oedema, and at good comfort levels for the mother. These are very beneficial outcomes.

The method according to the present invention advantageously permits the creation of the vacuum in the second chamber quickly and efficiently by virtue of the connection of the second chamber to the pump assembly and the reservoir, as compared to the second chamber being evacuated from atmosphere. By that connection, the second chamber is immediately or rapidly evacuated to the first vacuum pressure, which is the level of the vacuum within the reservoir and so the pump assembly is not required to evacuate the second chamber to that level. Instead, the pump assembly is only required to evacuate the second chamber from the first vacuum pressure to the second vacuum pressure. This saves time and pump effort. As an example, the first vacuum pressure in the inner chamber might be set at about −200 mmHg, while the second vacuum pressure for the second chamber might be set at about −380 mmHg. To reach −380 mmHg, the second chamber can be first evacuated to −200 mmHg via the connection of the second chamber to the pump assembly and the reservoir, without any effort by the pump assembly to evacuate the second chamber to that level. The pump assembly is then only required to increase the vacuum in the second chamber from −200 mmHg to −380 mmHg.

It is expected that there will be a vacuum pressure loss or drop in the reservoir upon the connection of the second chamber to the reservoir, but this can be minimised by the volume of the reservoir being much greater than the volume of second chamber. The normal size of breast milk reservoirs as used with prior art breastpump units is expected to be of a volume that meets this requirement of being much greater than the volume of second chamber.

The method according to the present invention also advantageously permits the reduction of the vacuum in the second chamber faster and more efficiently by the reverse process of connecting the second chamber to the reservoir whereby the greater second vacuum pressure will immediately or rapidly reduce to the first vacuum pressure without any pumping effort required. There will be a slight increase in pressure in the reservoir upon the connection of the second chamber to the reservoir, but again, this is minimised by the volume of the reservoir being much greater than the volume of second chamber.

Once the vacuum within the second chamber is at the first vacuum pressure of the reservoir, the pump assembly can operate to reduce the vacuum further as required, such as to atmosphere. Thus, the pump assembly is only required to decrease the vacuum from −200 mmHg to atmosphere, rather than from −380 mmHg to atmosphere.

As indicated above, the first vacuum pressure can be a substantially constant pressure, say of −200 mmHg. Step i. can thus involve bringing the inner chamber from atmosphere to −200 mmHg and then maintaining that vacuum for the duration of operation of the breastpump unit. The method of the invention can thus operate to evacuate the second or outer chamber of the breastpump unit from one vacuum level that is less than the first vacuum pressure, atmosphere for example, to the second vacuum pressure vacuum level that is greater than the first vacuum pressure. The method of the invention can thus switch the connection of the second chamber between connection with the reservoir and connection with atmosphere and advantageously, employs the vacuum in the reservoir for both vacuum generation and vacuum release, to increase the speed of vacuum generation and release and to reduce pump effort.

The examples given above give the first vacuum pressure as being about −200 mmHg and the second vacuum pressure as being about −380 mmHg. However, the vacuum pressures can be set at any level and so for example, the second vacuum pressure can be at least 25% higher than the first vacuum pressure or the second vacuum pressure can be approximately 75% higher than the first vacuum pressure. What is required is a differential between the vacuum pressures and so other ratios or values can be adopted. Other ratios or values might be appropriate for example for breast or nipple stimulation prior to breast milk expression, i.e. prior to the so-called let-down reflex. Suitable ranges for the for the first vacuum pressure include −70 to −350 mmHg, more preferably −120 to −200 mmHg. Suitable ranges for the second vacuum pressure include −150 to −480 mmHg, more preferably −250 to −380 mmHg.

The breastpump unit according to the invention facilitates the generation of pulses by the generation of the second vacuum pressure in the second chamber, in which the second vacuum pressure is a higher or greater vacuum than that in the inner chamber. The rapid generation of the second vacuum pressure allows the inner chamber expand and thus to partially or fully release the pressure applied to a nipple that has been inserted into the inner chamber. This cycle of squeezing and releasing the nipple has a positive effect on the expression of breast milk and is thought to be as a result of a massage effect that clears the milk ducts and that prevents or eliminates the formation of oedema. The effect is thought to more closely simulate infant suckling than existing breastpump units. The breast shield can also be constructed so that the pulse that is created also applies to the areola, so that there is also a massaging effect on that part of the breast. Again, the measured effect of massaging the areola is improved breast milk expression.

In some forms of the invention, once the second vacuum pressure has been reached, it can be released immediately to a lower pressure. However, in other forms of the invention, the second vacuum pressure is held substantially constant for a predetermined period in step ii prior to step iii. In either case, release of the second vacuum pressure to a lower pressure allows the inner chamber to exert increased compression on a nipple, by the inner chamber contracting under the influence of the first vacuum pressure. In other words, the at least partial release of the second vacuum pressure to a lower pressure allows the inner chamber to recover at least partially towards its relaxed or at rest state.

In some forms of the invention, the lower pressure of step iii is atmospheric pressure. However, in other forms of the invention, the lower pressure of step iii is still a negative pressure which is either reduced to less than the vacuum pressure of the inner chamber, or which is reduced but greater the vacuum pressure of the inner chamber. Reduction of the second vacuum pressure to atmospheric pressure in step iii is convenient and relatively easy from an operational point of view, but the present invention is being developed to provide for use across a wide spectrum of physical parameters such as relating to the dimensions of the breast and nipple and parameters relating to sensitivity and comfort of the mother, so that the reduction of the second vacuum pressure to atmospheric pressure in step iii is not always expected to be undertaken.

While the pressure levels discussed above can vary to obtain the most efficient breast milk expression, the time periods for each step can also vary. In some forms of the invention tested to date, beneficial results have been realised when the duration of step i. is about 540 ms, the duration of step ii. is about 440 ms and the duration of step iii. is about 540 ms. In some forms of the invention, the cumulated durations of steps ii and iii can be in the region of around 900 ms (at 54 cycles per minute) +/−200 ms. This cumulated duration can also apply when the cycle includes the period of holding the second vacuum pressure substantially constant in step ii prior to step iii. The preferred ratio during current testing of the duration of step ii and step iii is inbetween 3/7 to 4/6. These time periods can of course vary as required and as further testing reveals advantageous vacuum levels and time periods for application.

In some forms of the invention, the pump assembly includes a single vacuum pump and the method of operating a breastpump unit according to the invention includes a valve assembly, such as a switching valve, in particular a solenoid valve to facilitate in step i., connecting the inner chamber and the reservoir in series to the inlet of the vacuum pump and connecting the second chamber to atmosphere, and in step ii., switching the valve to switch the second chamber into connection with the inlet of the vacuum pump and to switch the inner chamber and the reservoir into connection with the outlet of the vacuum pump. Step iii., can return the switching valve back to the position in step i.

In other forms of the invention, the pump assembly includes a single vacuum pump and the method of operating a breastpump unit according to the invention includes in step i., the inner chamber and the reservoir being connected in series to the inlet of the vacuum pump via a first valve, and the second chamber being connected to atmosphere via a second valve, and in step ii., the first and second valves being closed and inner chamber and the reservoir being connected in series to the outlet of the vacuum pump via a third valve and the second chamber being connected to the inlet of the vacuum pump via a fourth valve. Step iii., can return the first and second valves back to the respective positions in step i.

In some forms of the invention, the pump assembly includes a pair of vacuum pumps arranged so that the inner chamber and the reservoir are connected in series to the inlet of a first of the vacuum pumps and the second chamber is connected to the inlet of a second of the vacuum pumps via a first valve, a pressure line extends between the inlet of the first vacuum pump and the outlet of the second vacuum pump and includes a second valve, and the method of operating a breastpump unit according to the invention includes in step i., opening the first valve to atmosphere and closing the second valve to fluid passage, operating the first pump to evacuate the inner chamber and the reservoir to the first vacuum pressure, and in step ii., closing the first valve to atmosphere and opening the second valve to fluid passage and operating the second pump to evacuate the second chamber.

It will be evident that the method of the present invention can be carried out in various arrangements of vacuum pumps and valves. Specific examples are provided in the accompanying drawings.

It will also be evident that the present invention can be embodied in a breastpump unit for expression of human breastmilk, the breastpump unit having:
  a. a vacuum pump for generating pressure,
  b. a reservoir for receiving breastmilk, and
  c. a breast shield for sealing application to a breast to be pumped, the breast shield having an inner chamber for receiving a nipple of the breast and a second chamber, in particular an outer chamber extending about the outside of the inner chamber and which at least partially surrounds a nipple that is inserted into the inner chamber,
the breastpump unit being operable in a cycle in which:
  i. the vacuum pump evacuates the inner chamber and the reservoir to a first vacuum pressure,
  ii. the outer chamber connects to the vacuum pump and to the reservoir so that the outer chamber is evacuated to a second vacuum pressure, in which the second vacuum pressure is higher than the first vacuum pressure, and
  iii. vacuum in the outer chamber is at least partly released to a lower pressure, in particular lower than the first vacuum pressure.

In a breastpump unit according to the invention, the inner chamber can be defined by a flexible inner liner that includes an entry portion for receipt of a nipple and the second chamber being defined by a a stiff or rigid outer liner, the inner and outer liners defining the second chamber between them. The entry portion can have an internal diameter that is smaller than the outside diameter of the nipple that the breastpump unit is to be used with and the entry portion being expandable upon the introduction of vacuum in the inner chamber.

In some forms of the invention, the vacuum pump can have an inlet and an outlet and the breastpump unit can include a valve assembly inserted in the pressure lines extending from the inlet and the outlet. The valve assembly is operable to switch the inner chamber and the reservoir from pressure connection to the inlet of the vacuum pump to the outlet of the vacuum pump, and to switch the outer chamber from pressure connection to the outlet of the vacuum pump to the intlet of the vacuum pump. The valve assembly can be a switching valve, such as a 3/3 solenoid valve, or a 4/3 solenoid valve. Alternatively, the valve assembly can comprise four valves, each disposed in a separate pressure line.

DETAILED DESCRIPTION

Figure 1:
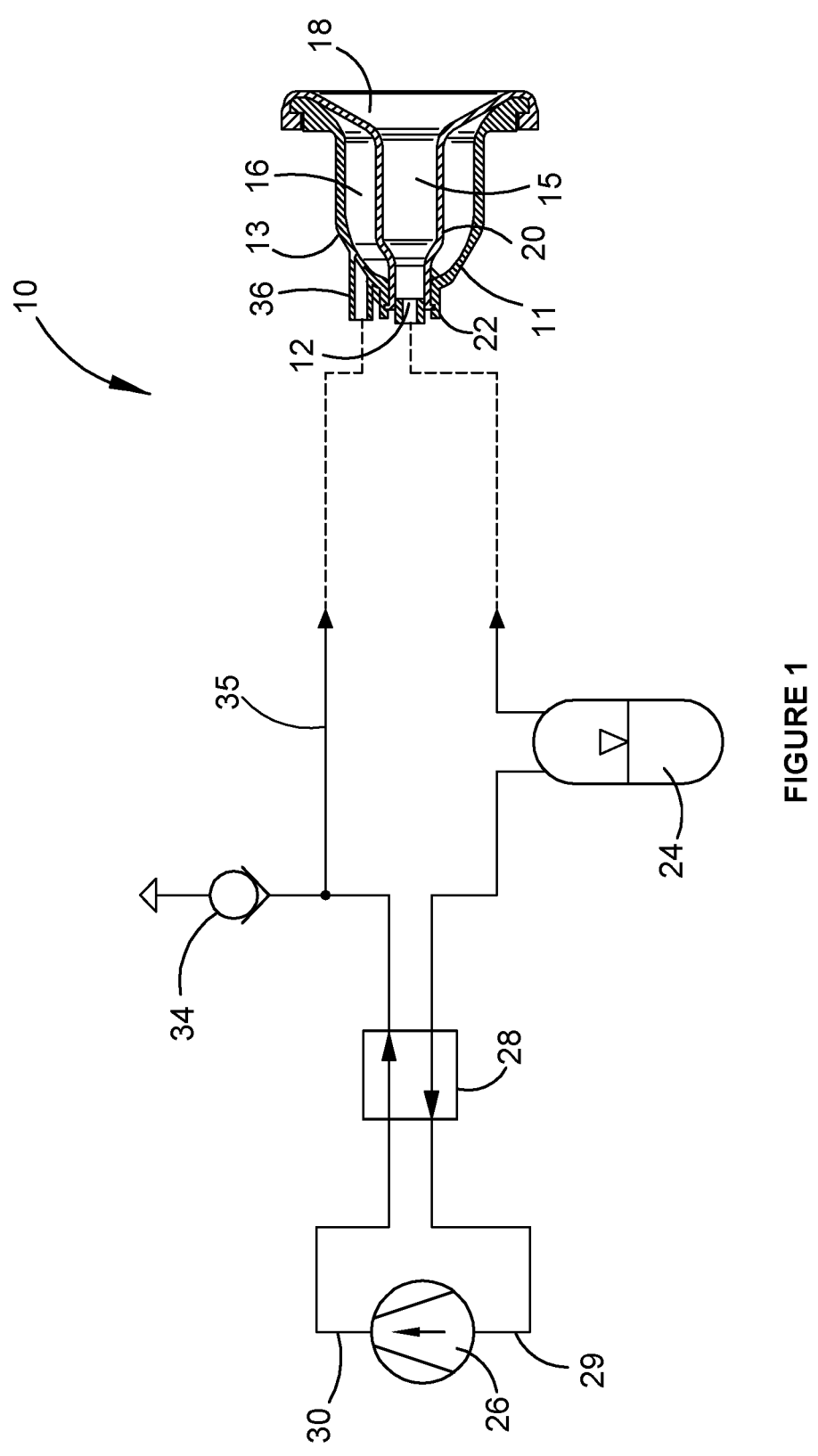
FIG. 1 schematically shows a breastpump unit used for the expression of human breastmilk when a valve thereof is in a first position.
Figure 2:
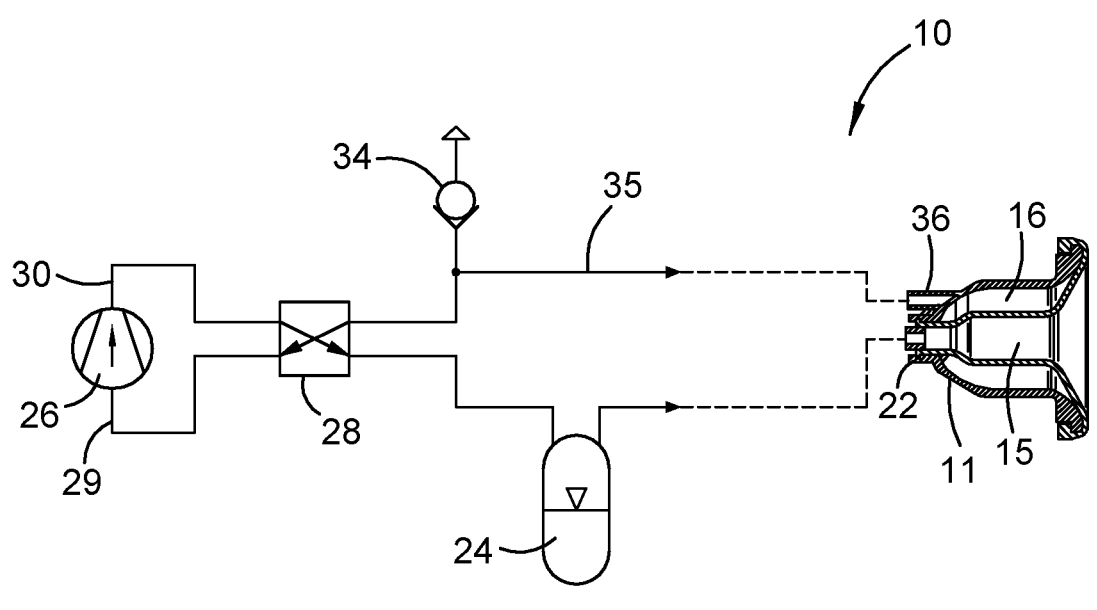
FIG. 2 schematically shows a breastpump unit used for the expression of human breastmilk after the valve thereof is switched to a second position.
Figure 3:
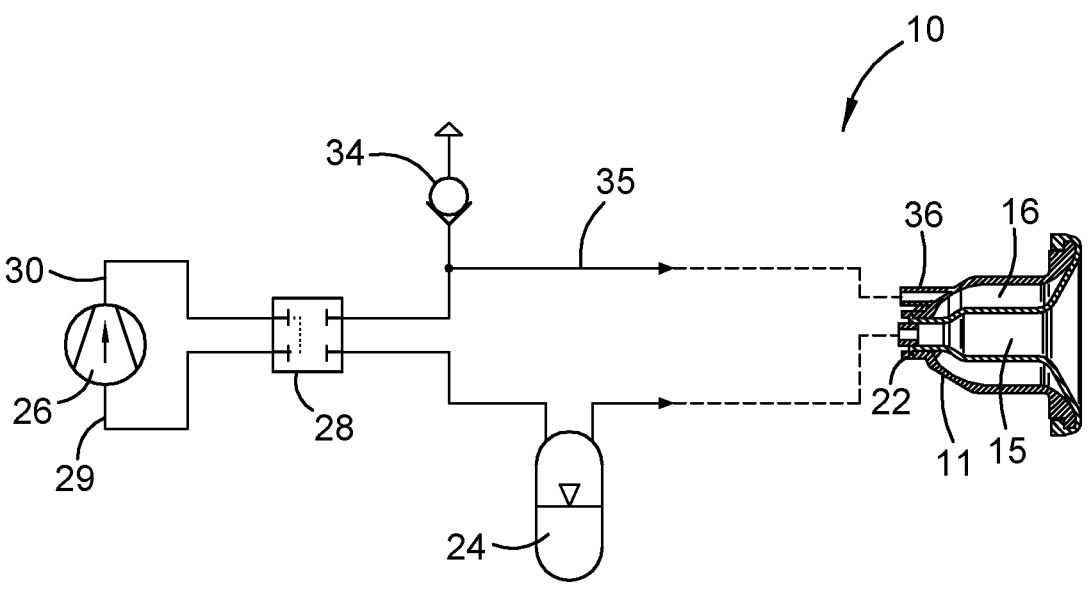
FIG. 3 schematically shows a breastpump unit used for the expression of human breastmilk after the valve thereof is switched to a third position.

FIGS. 1 to 3 schematically show a breastpump unit 10 for the expression of human breastmilk. The breastpump unit 10 includes a breastshield 11 that has a flexible annular inner liner 12 and a stiff or rigid outer annular liner 13. The inner liner 12 defines an inner chamber 15 for receiving a nipple of a breast and the outer liner 13 extends about the inner liner 12 and defines an outer chamber 16 extending about the outside of the inner chamber 15. The inner and outer liners 12 and 13 are connected at each end in a sealed manner so that a vacuum can be created in the outer chamber 16. The inner liner 12 includes a funnel portion 18 to seal against the surface of the mother's breast and a tubular entry portion 20 for receipt of a nipple. The inner diameter of the portion 20 is intended to be less than the outer diameter of the nipple that is inserted into the portion 20, so that the portion 20 compresses or squeezes the nipple at rest or in a relaxed state of the inner liner 12. As will be explained later herein, the compression or squeezing pressure that is applied to a nipple by the portion 20 of the inner liner 12 can be reduced or released by vacuum introduced into the outer chamber 16. By cyclic variation of the pressure or vacuum within the outer chamber 16, the nipple can be compressed and relaxed cyclically for the purpose of breastmilk extraction. Also, the funnel portion 18 will rest against the areola of the breast when the breastshield 11 is applied to a breast and the vacuum that is introduced into the outer chamber 16 will also cause the funnel portion 18 to shift or vibrate on the areola, thus massaging the areola and assisting the commencement of milk expression as well as overall improved breast milk expression.

The inner liner 12 has an evacuation port 22 about which the outer liner seals. The evacuation port 22 connects to a reservoir 24, which in the embodiment illustrated is a collection reservoir for receiving breastmilk. The reservoir 24 connects to a vacuum pump 26 via a valve 28. The valve 28 connects to the inlet 29 and outlet 30 of the vacuum pump 26 and in the orientation of the valve 28 in FIG. 1 shown by the arrows, the reservoir 24 connects to the inlet 29 of the valve 28 and the outlet 30 of the valve 28 connects to atmosphere via a one-way check valve 34.

A pressure line 35 also connects to an evacuation port 36 of the outer liner 13, however in the orientation of the valve 28 in FIG. 1, fluid (air) that is evacuated by the vacuum pump 26 from the inner chamber 15 and the reservoir 24 and that is discharged through the outlet 30 of the pump 26, is exhausted through the check valve 34 to atmosphere.

The vacuum pump 26 thus generates a vacuum in each of the inner chamber 15 and the reservoir 24 to a predetermined level. In testing to date, one predetermined level has been –200 mmHg.

Once at the selected predetermined vacuum level, the valve 28 is switched to the position shown in FIG. 2. In that position, the pressure line 35 connects to the inlet 29 of the vacuum pump 26 and the outlet 30 of the vacuum pump 26 is connected to the reservoir 24 and the inner chamber 15. The outlet 30 of the vacuum pump 26 thus is almost instantaneously taken from atmospheric pressure to the predetermined vacuum level to which the reservoir 24 and the inner chamber 15 have been pumped. This switching also results in the outer chamber 16 being almost instantaneously evacuated to the predetermined vacuum level. The vacuum pump 26 can now continue to evacuate the outer chamber 16 to a greater or higher vacuum level than that of the inner chamber 15 and the reservoir 24. The suction or vacuum pressure applied to the pressure line 35 also firmly closes the valve 34 so that the pressure line 35 is closed to atmosphere. In prototype testing to date, one greater or higher vacuum level to which the outer chamber 16 has been evacuated is –380 mmHg.

When the valve 28 is switched from the position shown in FIG. 1 to that of FIG. 2, there will be a pressure loss or drop in the reservoir 24 and the inner chamber 15, but this is minimised by the volume of the reservoir 24 and the inner chamber 15 being much greater than the volume of outer chamber 16. The ratio can be in the region of 1:10 or above.

There will also be a small loss of pressure by the entry of breast milk into the reservoir 24, but again, this is minimised by the volume of the reservoir 24 and the inner chamber 15 being much greater than the volume of outer chamber 16.

FIG. 3 illustrates a further position of the valve 28, in which each of the inner chamber 15, the outer chamber 16 and the reservoir 24 are isolated from the vacuum pump 26 so that the vacuum pressures generated are held or maintained for a predetermined period. Once the predetermined period has expired, the valve 28 can switch back to the FIG. 1 position. In that position, the inner chamber 15 and the reservoir 24 will return to direct connection with the inlet 29 of the vacuum pump 26 and so will be returned to the predetermined vacuum level previously described, while the outer chamber 16 will return to atmospheric pressure. Correction of the loss in pressure in the reservoir 24 is facilitated by exhaust of fluid from within the reservoir 24 through the check valve 34.

Figure 4:
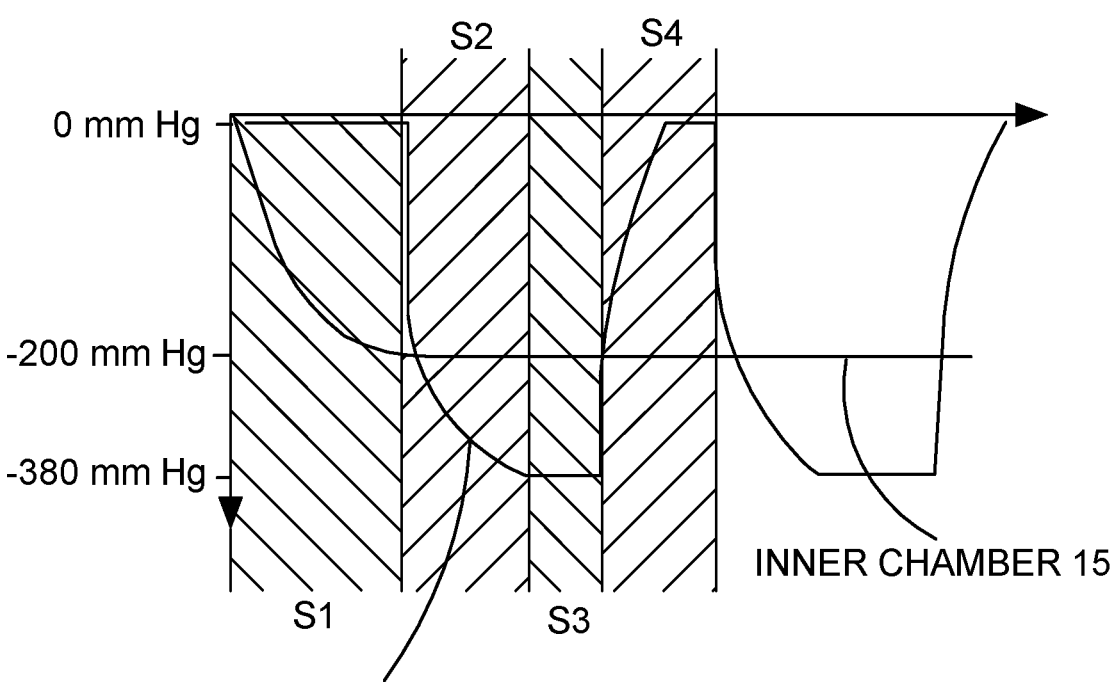
FIG. 4 is a graph of the vacuum pressure created in the inner and outer chambers of the breastpump unit of FIG. 1

The sequence of operation of the breastpump unit 10 shown in FIGS. 1 to 3 can be cycled to create a pulsating movement within the breastshield 11 to extract breast milk. An approximate graph of the pressure created in the inner and outer chambers 15, 16 is shown in FIG. 4. The graph illustrates vacuum pressure (Y axis) versus time (X axis). The line marked 'inner chamber 15' commences at atmospheric pressure and lowers to a generally constant negative or vacuum pressure. The line marked 'outer chamber 16' is cyclic as illustrated.

Section 1 of the cycle shown in FIG. 4 as S1 is the section in which the valve 28 is in the FIG. 1 position, so that the inner liner is evacuated from atmosphere to a predetermined pressure level, such as −200 mmHg. In section 1, the outer chamber 16 within the outer liner 13 is maintained at atmosphere. In section 2 (S2), the valve 28 has been switched to the FIG. 2 position so that pressure within the outer chamber 16 increases, such as to −380 mmHg. Importantly, the graph shows that the vacuum in the outer chamber 16 increases immediately from 0 mmHg to close to the −200 mmHg vacuum in the inner chamber 15 and then increases more gradually or slowly from −200 mmHg to −380 mmHg. This reflects that as soon as the valve 28 is switched from the position of FIG. 1 to the position of FIG. 2, the outer chamber 16 is connected via the inlet 29 of the vacuum pump 26 to the reservoir 24 so that the outer chamber 16 is almost instantaneously taken from atmospheric pressure to the −200 mmHg vacuum pressure within the reservoir 24. The graph also shows that the vacuum pump 26 then works to further evacuate the outer chamber 16 to −380 mmHg, but that this takes more time.

As indicated above, there will also be a slight pressure drop in the inner chamber 15 when the valve 28 is switched to the FIG. 2 position, but this can be relatively small so as not to be readily apparent in the graph of FIG. 2. In section 3 (S3), the valve 28 has been switched to the FIG. 3 position so that the pressure within the outer chamber 16 is maintained without increasing or decreasing. Finally, section 4 (S4) is where the valve 28 switches back to the FIG. 1 position, whereby the outer chamber 16 is exhausted to atmosphere, but the inner chamber 15 is retained under vacuum. In section S4, the graph again shows an almost instantaneous reduction of vacuum pressure from −380 mmHg to −200 mmHg, which occurs as a result of connecting the outer chamber 16 to the reservoir 24 via the vacuum pump 26 so as to immediately or rapidly reduce pressure in the outer chamber 16 to the vacuum pressure in the reservoir 24 without any pumping effort required. Pumping effort is then required to evacuate the outer chamber 16 to atmosphere, which as shown in section S4, takes more time.

Importantly, the cycle does not return the inner chamber 15 back to atmosphere, but rather, the vacuum within the inner chamber 15 is maintained generally constant once the inner chamber 15 has initially been evacuated. That is, the cycle does not return to section 1 of FIG. 4, but cycles through sections 2 to 4. This constant vacuum pressure draws breast milk through the nipple and into the reservoir 24.

In relation to the action of the breastshield 11 on the breast and nipple, as explained above, the diameter of the inner liner 12 at the entry end or tubular portion 20 within which a nipple is inserted can be made to be smaller and potentially much smaller than the outside diameter of the nipple, so that in the relaxed state of the inner liner 12, an inserted nipple is compressed or squeezed. That compression is maintained through section S1. However, when vacuum is generated in the outer chamber 16 in section S2, the tubular portion 20 reduces or releases pressure on the nipple. This occurs because, upon the generation of vacuum in the outer chamber 16 to levels that are greater than within the inner liner 12, the inner liner 12 expands and thus applies progressively less pressure against the nipple until eventually the vacuum in the outer chamber 16 will be sufficient that the inner liner 12 actually loses (at least partially) contact with the nipple surface so that no compression or squeezing pressure is acting on the nipple. This arrangement is achieved by the outer liner 13 being stiff or rigid, and the inner liner 12 being flexible. The vacuum cycle is thus such as to cyclically compress and release the nipple.

The compression or squeezing pressure applied to the nipple is reduced or released for the part of the section S2 when the vacuum generated in the outer chamber 16 exceeds the vacuum generated in the inner chamber 15 and for all of section S3. The vacuum pressure within the outer chamber 16 reduces to a point below that of the inner chamber 15 in section 4, so allowing the portion 20 of the inner liner 12 to return to contract to a compressing or squeezing position on the nipple.

It will be understood from FIG. 4 that the vacuum that is applied to the inner chamber 15 is generally constant once the pressure has reached the predetermined level. That vacuum draws milk from the nipple and transports that milk to the reservoir 24. It will be further understood that the cyclic vacuum that is applied to the outer chamber 16 results in the tubular portion 20 expanding and contracting so as to release then squeeze a nipple inserted within the tubular portion 20. This effect of releasing and squeezing the nipple cyclically induces the expression of milk from the breast.

In addition, the outer liner 13 also applies and releases pressure against the inner liner 12 at the funnel portion 18 of the inner liner 12 and that application and release of pressure at the funnel portion 18 tends to massage the areola portion of the breast which likewise is understood to assist both the commencement of milk expression (often referred to as "let-down") and the continuation of milk expression.

The duration of the different sections of the cycle illustrated in FIG. 4 can be selected as required, or as testing indicates to be optimal. In some testing conducted to date, the periods for sections S1 to S4 are 540 ms, 440 ms, 300 ms and 540 ms.

The present invention differs from the arrangement of EP 3 027 240 at least by the operation of the system to maintain pressure within the inner chamber 15 and the reservoir 24 while pressure within the outer chamber 16 is varied between atmosphere and maximum vacuum. The arrangement of FIGS. 1 to 4 facilitates vacuum within the outer liner 13 to pulsate to generate the application and release of pressure to the nipple and the areola of a breast. The arrangement of the invention advantageously benefits from the pressure initially generated in the reservoir 24 for both the evacuation of the outer chamber 16 to a pressure greater than that in the inner chamber 15, and for the return of the pressure in the outer chamber 16 to atmosphere. In this respect, the system of the present invention rapidly brings the pressure in the outer chamber 16 equal to the pressure of the reservoir 24 when the evacuation port 36 of the outer chamber 16 is connected to the inlet 29 of the vacuum pump 26 and only at that stage is the pump 26 required to work to increase the vacuum pressure in the outer chamber 16 further. In addition, when the vacuum in the outer chamber 16 is to be released back to atmosphere, reconnection of the outer chamber 16 to the outlet 30 of the pump 26 rapidly reduces the pressure within the outer chamber 16 back to equal with the reservoir 24 and only at that stage is the pump 26 required to work to decrease the vacuum pressure in the outer chamber 16 further (to atmospheric levels). Advantageously, the increase of vacuum pressure within the outer chamber 16 from atmosphere to equal with the reservoir 24 and then the decrease from greater than the reservoir 24 back to equal with the reservoir 24, occurs rapidly in either direction.

Moreover, re-pressurising or re-vacuumising the reservoir 24 in section S4 of FIG. 4 is rapid as it takes place against the vacuum maintained in the inner chamber 15, rather than commencing from atmosphere.

Still further, any air that has leaked into the system is removed through the check valve 34 as the reservoir 24 is re-pressured and this stabilises the cycle during long periods of operation.

Figure 5:
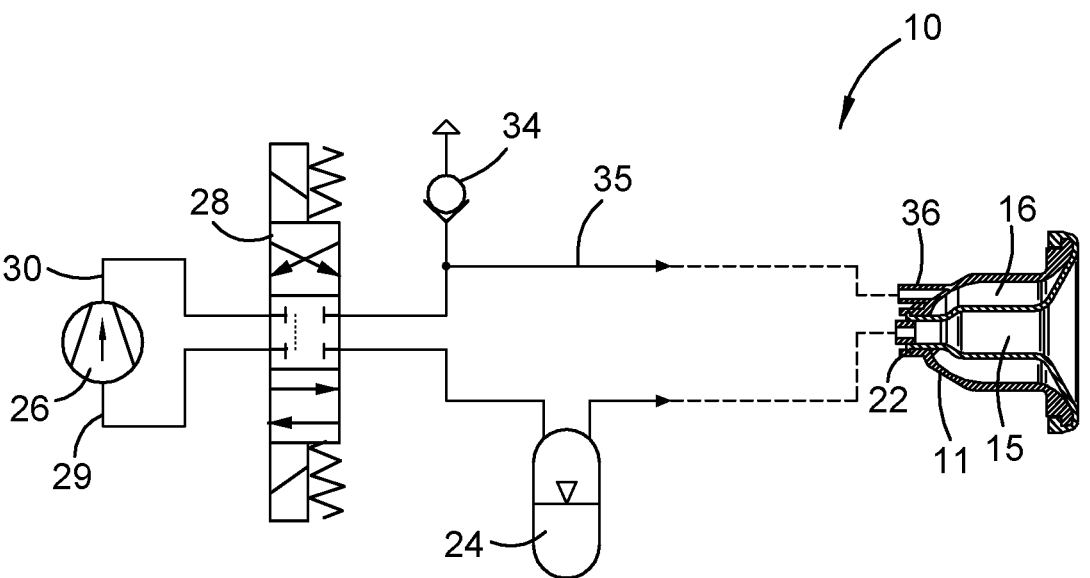
FIG. 5 schematically shows an alternative breastpump unit used for the expression of human breastmilk, wherein the valve is a 4/3 solenoid valve.

FIG. 5 shows the arrangement of FIGS. 1 to 3 with the valve 28 shown as a 4/3 solenoid valve, i.e. a four way, three position directional control valve. FIG. 5 shows how the valve 28 can switch by linear movement between the stages described in relation to FIGS. 1 to 3.

Figure 6:
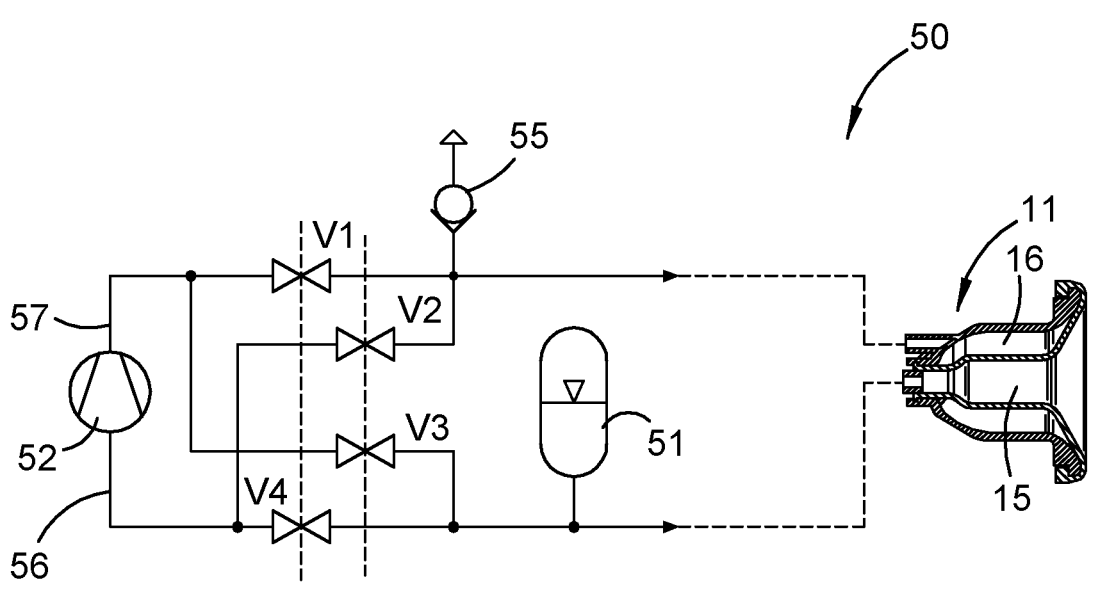
FIG. 6 schematically shows another alternative breastpump unit used for the expression of human breastmilk, including four separate valves.

FIG. 6 is a further schematic illustration of an alternative arrangement that employs four separate valves. FIG. 6 illustrates the breast shield 11 of the earlier embodiments employed within a breastpump unit 50 that includes a reservoir 51 (a milk bottle), a vacuum pump 52, valves V1 to V4, and a one-way check valve 55.

The valves V1 to V4 are controlled by a suitable control mechanism that can selectively open and close the valves. The control mechanism is not shown in FIG. 6 but would be readily available and understood by a person skilled in the art.

The vacuum pump 52 has an inlet 56 and an outlet 57. The valves V1 to V4 operate to switch the inlet 56 and outlet 57 between the reservoir 51 and the outer chamber 16 of the breast shield 11. The breastpump unit 50 can be operated to produce the pressure graph of FIG. 4 by initially opening valves V1 and V4 and closing valves V2 and V3. In this state, the inner chamber 15 of the breast shield 11 and the reservoir 51 are connected to the inlet 56 of the pump 52, while the outlet 57 can exhaust through the check valve 55. Operation of the pump 52 thus evacuates the inner chamber 15 and the reservoir 51.

Once the predetermined pressure level in the inner chamber 15 and the reservoir 51 has been reached, valves V1 and V4 can be closed and simultaneously, valves V2 and V3 can be opened. Alternatively, all of the valves V1-V4 could be held closed for a very short time, 5-10 ms for example, before opening valves V2 and V3, to ensure correct transition of pressure between the respective pressure lines controlled by the valves V1 to V4.

This switches the pressure lines so that the outer chamber 16 of the breast shield 11 connects to the inlet 56 of the pump 52 and the reservoir 51 and inner chamber 15 connect to the outlet 57. This immediately and rapidly generates a vacuum within the outer chamber 16 to a level equal with that in the reservoir 51, with a very slight reduction in vacuum occurring in the reservoir 51.

The use of four valves in FIG. 6 as opposed to the single form of solenoid valve shown in the earlier figures, produces the same result as described in relation to the breastpump unit 10, although the control of the four valves will be different and will employ different circuitry and hardware.

Figure 7:
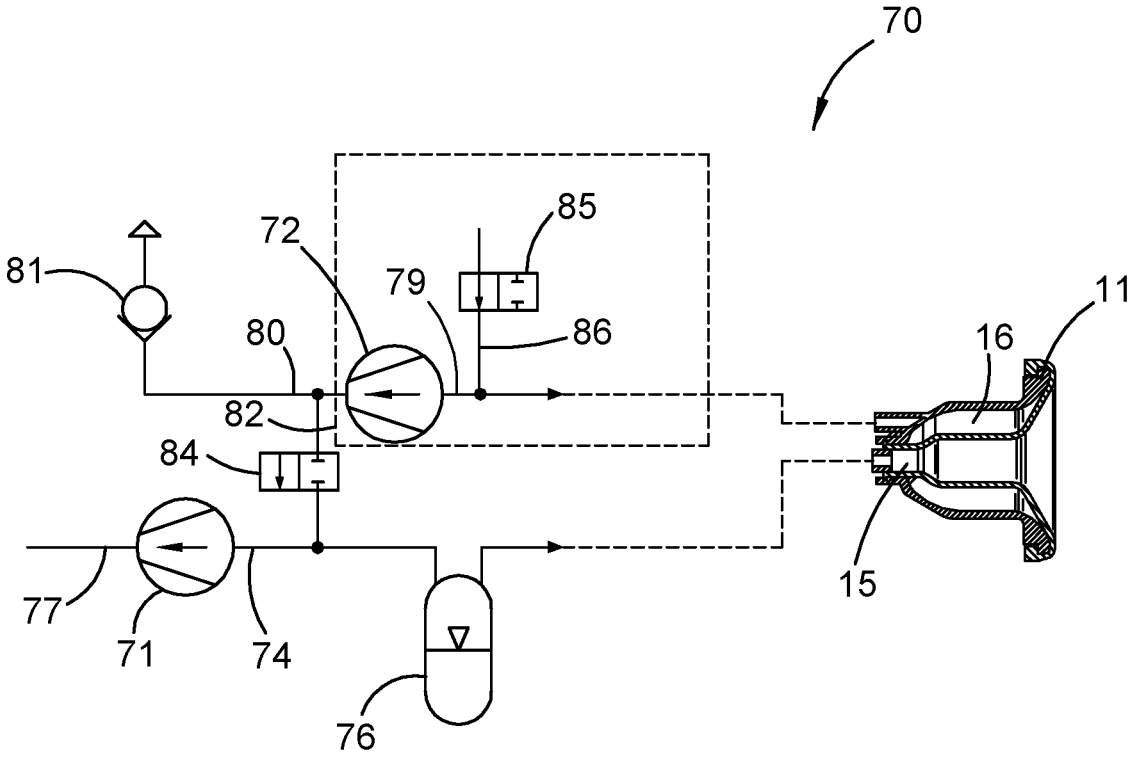
FIG. 7 schematically shows another alternative breastpump unit used for the expression of human breastmilk, employing first and second valve pumps and a 2/2 solenoid valve.

FIG. 7 is a further alternative arrangement to achieve the same pressure graph as shown in FIG. 4, but the breastpump unit 70 of FIG. 7 employs first and second vacuum pumps 71 and 72, rather than a single vacuum pump of the earlier figures. In FIG. 7, the inlet 74 of the vacuum pump 71 connects to the reservoir 76 and to the inner chamber 15 of the breast shield 11. The outlet 77 of the pump 71 connects to atmosphere.

The inlet 79 of the vacuum pump 72 connects to the outer chamber 16 of the breast shield 11, while the outlet 80 connects through a one-way check valve 81 to atmosphere.

A pressure line 82 extends between the inlet 74 of the pump 71 and the outlet 80 of the pump 72. A 2/2 solenoid valve 84 controls pressure flow through the line 82.

A further 2/2 solenoid valve 85 is disposed within a pressure line 86 on the inlet side of the pump 72 and controls flow through the pressure line 86 to atmosphere.

With the position of the valves 84 and 85 as shown in FIG. 7, both of the vacuum pumps 71 and 72 can be operated at the same time with the effect that pump 71 evacuates the inner chamber 15 and the reservoir 76, while pump 72 draws air through the valve 85 and exhausts that air back through the valve 81 to atmosphere. It will be appreciated that the pump 72 need not be operating during initial operation of the pump 71 to evacuate the inner chamber 15 and the reservoir 76, but the alternative is to run the pump 72 continuously. This can be advantageous given the short cycle times that the breastpump unit 70 operates under, which might be compromised if the pump 72 is switched on and off cyclically. The state that is reached in FIG. 7 is the section S1 of FIG. 4.

Once the vacuum pressure in the inner chamber 15 and the reservoir 76 has reached a predetermined vacuum level (−200 mmHg for example), the valves 84 and 85 are switched, so that the valve 84 facilitates or allows flow from the outlet 80 of the pump 72 to the inlet 74 of the pump 71 and the valve 85 is closed against passage of air to atmosphere. In these switched positions, the breastpump unit 70 enters the section S2 of FIG. 4 in which the outlet 80 of the pump 72 is connected to the inlet 74 of the pump 71 and so the outlet 80 of the pump 72 is immediately taken to the vacuum pressure at the inlet 74. It follows that the outer chamber 16 is also immediately taken to that pressure. The pump 72 can then further increase the vacuum pressure in the outer chamber 16 starting from the vacuum pressure of the reservoir 76.

Once the vacuum in the outer chamber 16 has reached the greater vacuum pressure required (at the end of section S2 in FIG. 4), the valve 84 can be returned to the closed position shown in FIG. 7, noting that the valve 85 has already switched to that closed position in section S2. The breastpump unit 70 is now in section S3.

Finally, to return the vacuum within the outer chamber 16 to atmosphere, the valves 84 and 85 return to the positions shown in FIG. 7 whereby the outer chamber 16 is exhausted to atmosphere, but the inner chamber 15 remains under vacuum. By returning to the valve positions of FIG. 7, the outer chamber 16 will immediately drop to the predetermined vacuum level present in the reservoir 76 and once at that level, the pump 72 operates to lower the vacuum within the outer chamber 16 to atmosphere.

Figure 8:
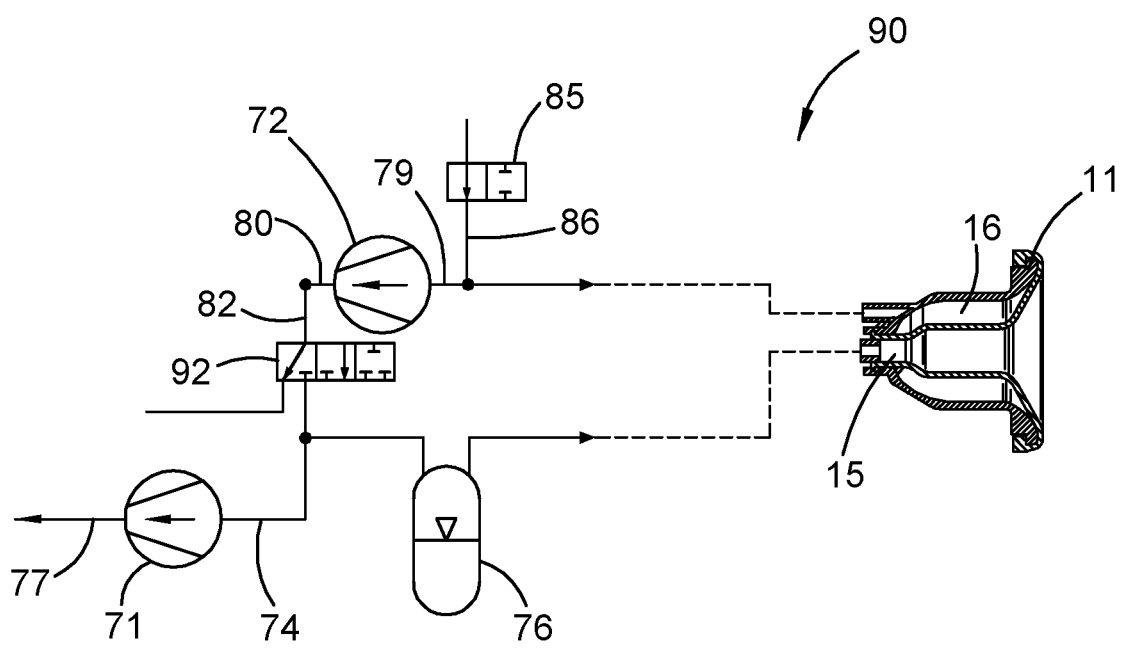
FIG. 8 schematically shows another alternative breastpump unit used for the expression of human breastmilk similar to that of FIG. 7, but wherein the valve is a 3/3 solenoid valve.

FIG. 8 shows a further alternative arrangement of a breastpump unit 90 that employs the breast shield 11 of the earlier figures. The FIG. 8 arrangement is very similar to the breastpump unit 70 of FIG. 7 with the exception that a 3/3 solenoid valve is employed in place of the 2/2 solenoid valve 84 of FIG. 7. The same reference numerals used in FIG. 7 are therefore used in FIG. 8 to denote the same or common parts between the respective breastpump units 70 and 90.

In FIG. 8, the 3/3 solenoid valve 92 is shown for operation in section S1 of FIG. 4, by the vacuum pump 71 drawing a vacuum from the inner chamber 15 of the breast shield 11 and from the reservoir 76. The valve 92 closes the path through the pressure line 82 and so if the vacuum pump 72 is also running, it takes air in through the pressure line 86 and discharges it through the pressure line 82 through the valve 92 to atmosphere.

Once the vacuum pressure in the inner chamber 15 and the reservoir 76 has reached a predetermined vacuum level, the valves 85 and 92 can be shifted, so that the valve 85 closes the pressure line 86 to atmosphere and the valve 92 opens the pressure line 82 between the outlet 80 of the pump 72 and the inlet 74 of the pump 71. As with the earlier embodiments, this valve movement shifts the inlet of the outer chamber 16 to the pressure at the inlet 74 of the pump 71 and so the vacuum pressure within the outer chamber is immediately and rapidly reduced to the pressure within the reservoir 76. Continued evacuation of the outer chamber 16 via the pump 72 will continue to increase the vacuum within the outer chamber 16. This represents a section S2 of FIG. 4.

Once the vacuum in the outer chamber has reached the greater vacuum pressure required, the valve 94 can be switched to the closed position in which again, the pressure line 82 is closed. That brings the breastpump unit 90 to section S3 of FIG. 4.

Finally, the vacuum within the outer chamber 16 can be exhausted by returning the valves 85 and 92 to the positions shown in FIG. 8, whereby the outer chamber 16 is immediately lowered to the vacuum level present in the reservoir 76 and once at that level, the pump 72 can operate to continue to lower the vacuum within the outer chamber 16 to atmosphere.

Figure 9:
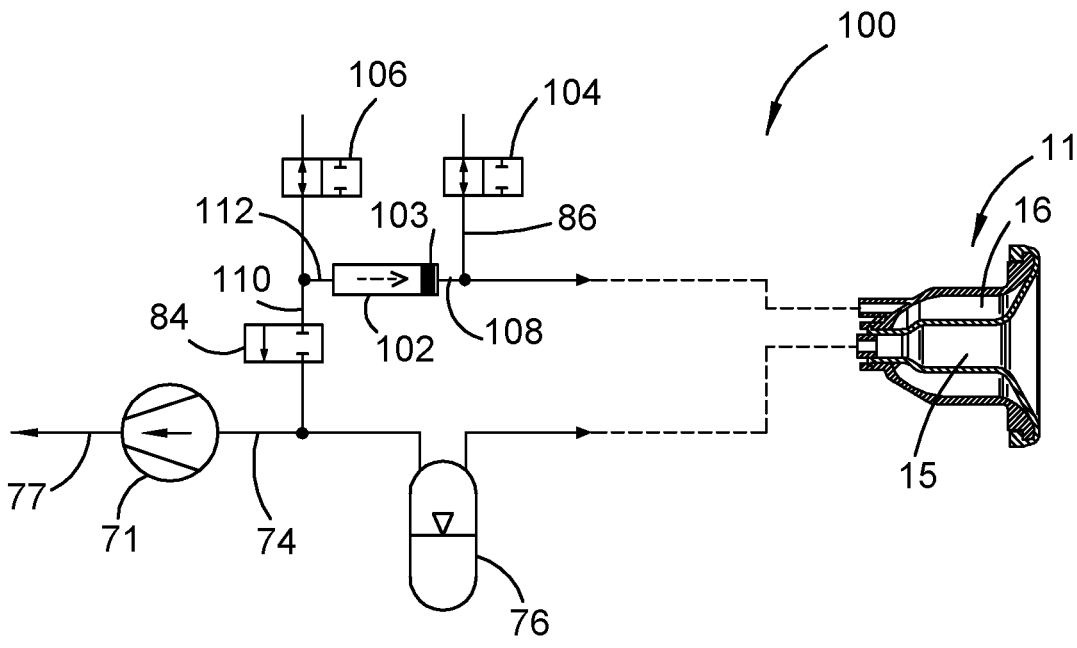
FIG. 9 schematically shows another alternative breastpump unit used for the expression of human breastmilk, employing a vacuum pump and reservoir, in which a second pumping facility thereof is a single stroke piston pump in communication with 2/2 solenoid valves.

FIG. 9 represents a further alternative arrangement of a breastpump unit 100 which employs a vacuum pump 71 and reservoir 76 in common with the earlier embodiments but the second pumping facility is a single stroke piston pump 102 that is in communication with 2/2 solenoid valves 104 and 106.

FIG. 9 illustrates section S1 of the pressure graph of FIG. 4 and in that state, the pump 102 has its piston 103 at the inlet end 108.

Figure 10:
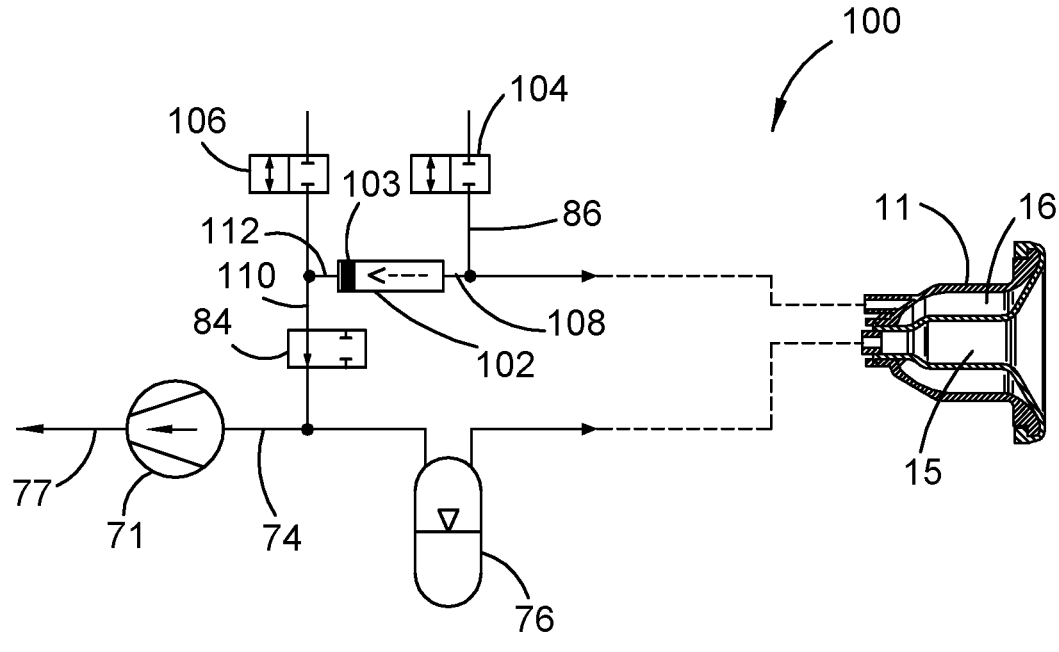
FIG. 10 schematically shows another alternative breastpump unit used for the expression of human breastmilk.

When the vacuum within the inner chamber 15 and the reservoir 76 has reached the predetermined level, the valves 104 and 106 can each be switched to closed positions and the valve 84 can be switched to open the pressure line 110. This state is shown in FIG. 10 in which the piston 103 of the piston pump 102 has travelled to the outlet end 112 to draw a vacuum into the outer chamber 16. The travel of the piston 103 within the pump 102 is such as to be able to create the required vacuum within the outer chamber 16.

Once the required vacuum is created within the outer chamber 16, the valve 84 is returned to the closed position of FIG. 9 and the respective vacuums are held constant through section S3 of FIG. 4.

When the outer chamber 16 is to be evacuated back to atmosphere, the valves 106 and 104 are returned to their open positions of FIG. 9 and the piston pump 102 can drive the piston 103 back to the inlet end 108 of the pump 102.

The figures illustrate various embodiments to achieve the pressure distribution within a breastshield as illustrated in FIG. 4. Other arrangements could be employed. However, each of the embodiments illustrated facilitates expansion and contraction of the inner liner 12, in particular the tubular portion 20 of the inner liner 12, to release and re-apply pressure to a nipple inserted into the tubular portion 20. Each of the embodiments also facilitates a massaging effect on the areola of the breast, which testing indicates assists the commencement of milk expression as well as overall improved breast milk expression. The physical testing undertaken with lactating mothers also indicates that the manner in which the breastshield moves provides improved comfort to the mother, so that mothers are more likely to express breastmilk over a longer period, rather than reverting to milk formula, to the benefit of the newborn infant.

Where any or all of the terms "comprise", "comprises", "comprised" or "comprising" are used in this specification (including the claims) they are to be interpreted as specifying the presence of the stated features, integers, steps or components, but not precluding the presence of one or more other features, integers, steps or components.

Those skilled in the art will appreciate that the invention described herein is susceptible to variations and modifications other than those specifically described. It is understood that the invention includes all such variations and modifications which fall within the spirit and scope of the present invention.

Future patent applications may be filed in Australia or overseas on the basis of or claiming priority from the present application. It is to be understood that the following provisional claims are provided by way of example only, and are not intended to limit the scope of what may be claimed in any such future application. Features may be added to or omitted from the provisional claims at a later date so as to further define or re-define the invention or inventions.

The invention claimed is:

1. A method for operating a breastpump unit for expression of human breastmilk, the breastpump unit having:
   a. a pump assembly for generating vacuum pressure,
   b. a reservoir for receiving breastmilk, and
   c. a breast shield for sealing application to a breast to be pumped, the breast shield having a flexible inner chamber for receiving a nipple of the breast and a second chamber, comprising an outer chamber extending about the outside of the inner chamber and which at least partially surrounds a nipple that is inserted into the inner chamber,
   the method comprising a cycle including, in order,
   i. first, evacuating the inner chamber and the reservoir by the pump assembly to a first vacuum pressure,
   ii. next, connecting the second chamber to the pump assembly and to the reservoir and evacuating the second chamber to a second vacuum pressure, in which the second vacuum pressure is higher or greater than the first vacuum pressure, and
   iii. then, at least partly releasing the vacuum from the second chamber to a lower vacuum pressure.

2. The method according to claim 1, the first vacuum pressure being a substantially constant pressure.

3. The method according to claim 1, the second chamber being connected to the vacuum pump and to the reservoir once the inner chamber has been evacuated to the first vacuum pressure.

4. The method according to claim 1, the second vacuum pressure being at least 25% higher than the first vacuum pressure.

5. The method according to claim 1, the second vacuum pressure being approximately −200 to −480 mmHg and the first vacuum pressure being approximately −70 to −350 mmHg.

6. The method according to claim 1, the first chamber including an entry portion into which a nipple can be inserted, the entry portion having an at rest or relaxed state in which it applies compressive pressure to the nipple and the entry portion expanding during step ii to reduce or completely release the compressive pressure.

7. The method according to claim 6, the entry portion returning to the at rest or relaxed state during step iii.

8. The method according to claim 1, the lower pressure of step iii being atmospheric pressure.

9. The method according to claim 1, the first vacuum pressure and the second vacuum pressure being held constant for a predetermined period in step iii. prior to step iii.

10. The method according to claim 1, the duration of step i. being about 540 ms, the duration of step ii. being about 440 ms and the duration of step iii. being about 540 ms.

11. The method according to claim 1,
   a. in step i., the inner chamber and the reservoir being connected in series to the inlet of the vacuum pump via a switching valve and the second chamber being connected to atmosphere,
   b. in step ii., switching the valve to switch the second chamber into connection with the inlet of the vacuum pump and to switch the inner chamber and the reservoir into connection with the outlet of the vacuum pump.

12. The method according to claim 1,
   a. in step i., the inner chamber and the reservoir being connected in series to the inlet of the vacuum pump via a first valve, and the second chamber being connected to atmosphere via a second valve
   b. in step ii., the first and second valves being closed and inner chamber and the reservoir being connected in series to the outlet of the vacuum pump via a third valve and the second chamber being connected to the inlet of the vacuum pump via a fourth valve.

13. The method according to claim 1, including a switching valve, wherein:
   a. in step i., connecting the inner chamber and the reservoir in series to the inlet of the vacuum pump and connecting the second chamber to atmosphere, and
   b. in step ii., switching the valve to switch the second chamber into connection with the inlet of the vacuum pump and to switch the inner chamber and the reservoir into connection with the outlet of the vacuum pump.

14. The method according to claim 1, including a single vacuum pump, wherein:
   a. in step i., the inner chamber and the reservoir being connected in series to the inlet of the vacuum pump via a first valve, and the second chamber being connected to atmosphere via a second valve, and
   b. in step ii., the first and second valves being closed and inner chamber and the reservoir being connected in series to the outlet of the vacuum pump via a third valve and the second chamber being connected to the inlet of the vacuum pump via a fourth valve.

15. The method according to claim 1, a pair of vacuum pumps arranged so that the inner chamber and the reservoir are connected in series to the inlet of a first of the vacuum pumps and the second chamber is connected to the inlet of a second of the vacuum pumps via a first valve, a pressure line extends between the inlet of the first vacuum pump and the outlet of the second vacuum pump and includes a second valve, the method including
   a. in step i., opening the first valve to atmosphere and closing the second valve to fluid passage, operating the first pump to evacuate the inner chamber and the reservoir to the first vacuum pressure, and
   b. in step ii., closing the first valve to atmosphere and opening the second valve to fluid passage and operating the second pump to evacuate the second chamber.

16. A breastpump unit for expression of human breastmilk, the breastpump unit having:
   a. a vacuum pump for generating pressure,
   b. a reservoir for receiving breastmilk, and
   c. a breast shield for sealing application to a breast to be pumped, the breast shield having a flexible inner chamber for receiving a nipple of the breast and a second chamber, in particular an outer chamber extending about the outside of the inner chamber and which at least partially surrounds a nipple that is inserted into the inner chamber,
the breastpump unit being operable in a cycle in which:
   i. the vacuum pump evacuates the inner chamber and the reservoir to a first vacuum pressure,
   ii. the outer chamber connects to the vacuum pump and to the reservoir so that the outer chamber is evacuated to a second vacuum pressure, in which the second vacuum pressure is higher than the first vacuum pressure, and
   iii. vacuum in the outer chamber is at least partly released to a lower pressure, in particular lower than the first vacuum pressure.

17. A breastpump unit according to claim 16, the inner chamber being defined by a flexible inner liner that includes an entry portion for receipt of a nipple and the second chamber being defined by a stiff or rigid outer liner, the inner and outer liners defining the second chamber between them.

18. A breastpump unit according to claim 17, the entry portion having an internal diameter that is smaller than the outside diameter of the nipple that the breastpump unit is to be used with and the entry portion being expandable upon the introduction of vacuum in the inner chamber.

19. The breastpump unit according to claim 16, the vacuum pump having an inlet and an outlet and the breastpump unit including a valve assembly inserted in the pressure lines extending from the inlet and the outlet, the valve assembly being operable to switch the inner chamber and the reservoir from pressure connection to the inlet of the vacuum pump to the outlet of the vacuum pump, and to switch the outer chamber from pump connection to the outlet of the vacuum pump to the inlet of the vacuum pump.

20. The breastpump unit according to claim 16, including first and second vacuum pumps in which the inlet of a first of the vacuum pumps connects to the reservoir and to the inner chamber and the outlet connects to atmosphere and the inlet of a second of the vacuum pumps connects to the second chamber and the outlet connects to atmosphere.

\* \* \* \* \*